US011419989B2

(12) United States Patent
Dumet et al.

(10) Patent No.: US 11,419,989 B2
(45) Date of Patent: Aug. 23, 2022

(54) REMOVAL MEMBER FOR REMOVING A NEEDLE PROTECTIVE CAP

(71) Applicant: Nemera La Verpillière, La Verpilliere (FR)

(72) Inventors: Clement Dumet, Vaulx en Velin (FR); Marc Todesco, Tignieu-Jameyzieu (FR); Pascal Dugand, Estrablin (FR); Jose Camba, Amberieu en Bugey (FR); Guillaume Abot, Trébeurden (FR)

(73) Assignee: Nemera La Verpillière

( * ) Notice: Subject to any disclaimer, the term of this patent is extended or adjusted under 35 U.S.C. 154(b) by 237 days.

(21) Appl. No.: 16/697,301

(22) Filed: Nov. 27, 2019

(65) Prior Publication Data

US 2020/0254189 A1 Aug. 13, 2020

(30) Foreign Application Priority Data

Nov. 27, 2018 (FR) ...................................... 1871946

(51) Int. Cl.
*A61M 5/32* (2006.01)
*A61M 5/20* (2006.01)
*A61M 5/315* (2006.01)

(52) U.S. Cl.
CPC ............ *A61M 5/3204* (2013.01); *A61M 5/20* (2013.01); *A61M 5/31501* (2013.01); *A61M 2005/2073* (2013.01)

(58) Field of Classification Search
CPC .... A61M 5/3204; A61M 5/32; A61M 5/3202; A61M 5/3205; A61M 5/3213;

(Continued)

(56) References Cited

U.S. PATENT DOCUMENTS 4,981,476 A 1/1991 Aichlmayr et al.
10,792,437 B2 * 10/2020 Holmqvist .......... A61M 5/3204
(Continued)

FOREIGN PATENT DOCUMENTS

EP 3257540 A1 12/2017
FR 3011186 A1 4/2015
(Continued)

OTHER PUBLICATIONS

Search Report from the French Patent Office for FR 1871946 dated Sep. 10, 2019 (2 pages).

*Primary Examiner* — Bhisma Mehta
*Assistant Examiner* — Phoebe Anne Staton
(74) *Attorney, Agent, or Firm* — St. Onge Steward Johnston & Reens LLC

(57) ABSTRACT

A removal member for removing a needle protective cap includes a housing having a longitudinal axis and receiving the cap along an insertion direction, the housing having a first support area and a second support area the first area being carried by a blocking element, movable relative to the housing between a cap insertion configuration, in which the orthogonal projections of the first and second areas in a transverse plane substantially perpendicular to the longitudinal axis are separated by an insertion distance, and a cap blocking configuration, in which the first and second areas are located in separate transverse planes, and in which the orthogonal projections of the first and second areas in said transverse plane are separated by a blocking distance less than the insertion distance and adapted to block the translation of the cap relative to the removal member in a removal direction opposite to the insertion direction.

17 Claims, 9 Drawing Sheets

(58) Field of Classification Search
CPC ........ A61M 5/3257; A61M 2005/3215; A61M 2005/3256; A61M 2005/3246; A61M 2005/3253; A61M 5/20; A61M 5/31501; A61M 2005/2073; A61M 5/321
See application file for complete search history.

(56) References Cited

U.S. PATENT DOCUMENTS

| 2014/0194827 A1* | 7/2014 | Hsu | A61M 5/3202 604/192 |
| 2015/0051553 A1* | 2/2015 | Bjork | A61M 5/3287 604/198 |

FOREIGN PATENT DOCUMENTS

| GB | 2469671 A | * 10/2010 | ......... A61M 5/3202 |
| GB | 2469671 A | 10/2010 | |
| WO | 2009081133 A1 | 7/2009 | |
| WO | 2015114318 A1 | 8/2015 | |

* cited by examiner

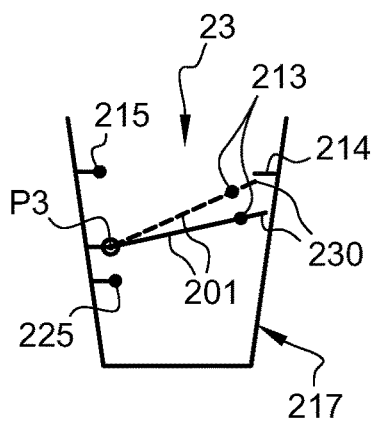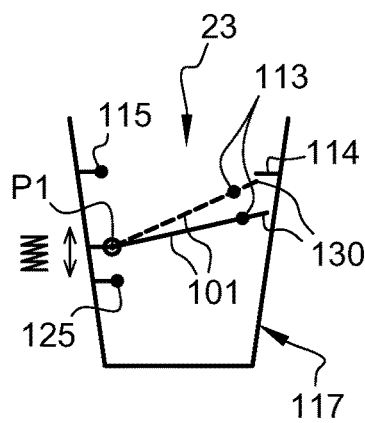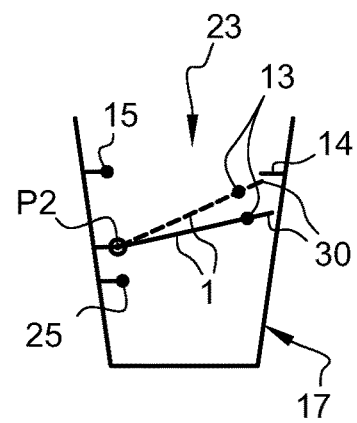
Fig. 3A  Fig. 3B  Fig. 3C
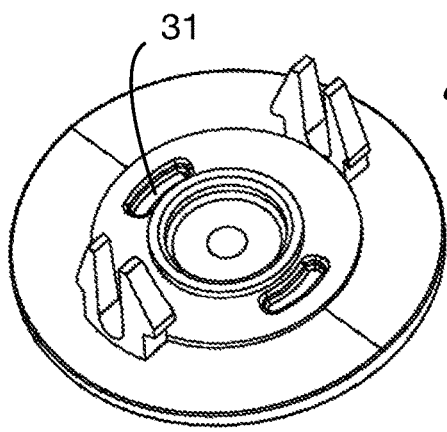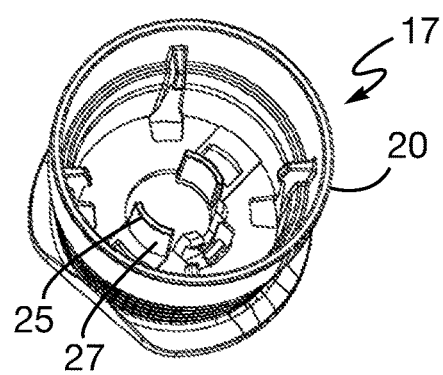
Fig. 4A  Fig. 4B
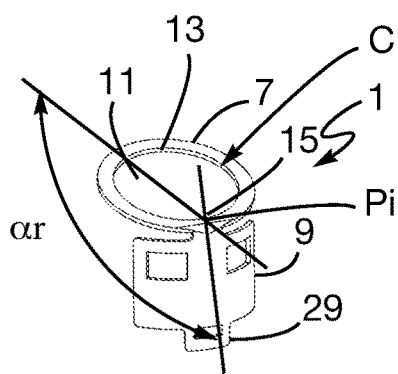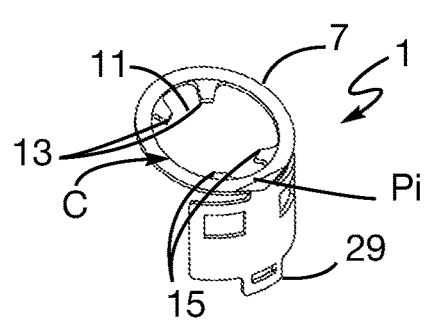
Fig. 5A  Fig. 5B

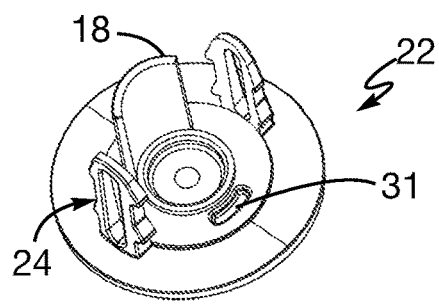
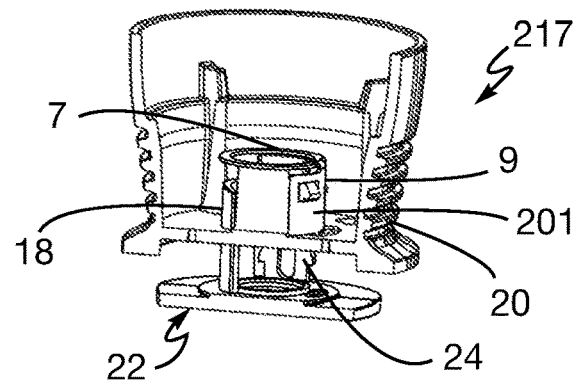
Fig. 13     Fig. 14
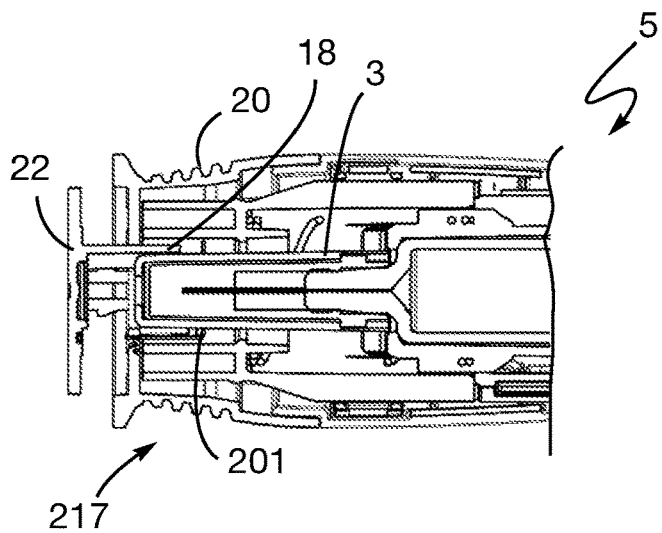
Fig. 15
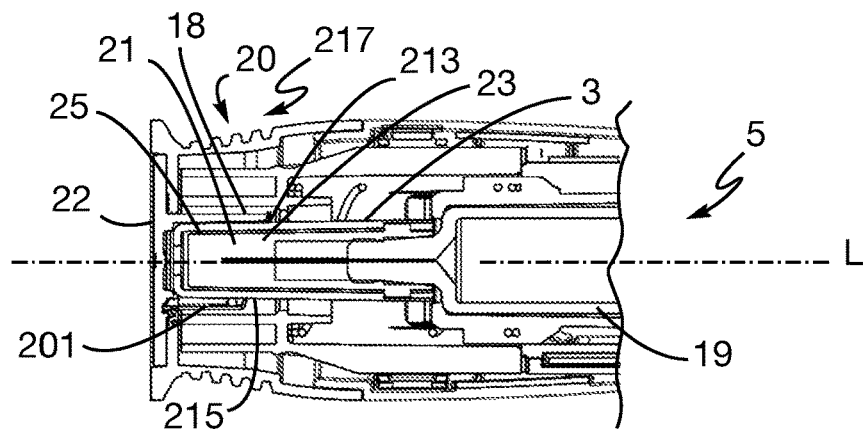
Fig. 16

REMOVAL MEMBER FOR REMOVING A NEEDLE PROTECTIVE CAP

FIELD OF THE INVENTION

The invention relates to a removal member for removing a needle protective cap, an injection device comprising such removal member, for example an injection syringe possibly comprising a safety device or an auto-injector device. It also relates to a method for assembling a removal member on an injection device. The removal member can be attached to the protective cap, such that removal of this member removes the protective cap.

BACKGROUND OF THE INVENTION

The invention relates more particularly to the removal, before injection, of the cap protecting the needle. The cap gripping area may be relatively small and, consequently, the cap may be difficult to remove, especially for persons suffering from polyarthritis. A removal member for removing the needle protective cap has already been proposed in application FR3011186. This removal member comprises elements for hooking the cap which grip behind it. To use this removal member, the injection device and the cap must be assembled so as to form, behind the cap, a space allowing the removal member to be hooked efficiently. Consequently, this removal member can only be used on injection devices having a suitable configuration.

The invention aims in particular to provide a removal member that can be used with more injection devices.

SUMMARY OF THE INVENTION

Thus, the invention relates in particular to a removal member for removing a needle protective cap, for an injection device comprising a needle and a removable needle protective cap, the removal member comprising a housing having a longitudinal axis and being adapted to receive the cap along an insertion direction, the housing being defined by at least first and second support areas called first and second areas intended to support the cap housed in the housing, the first area being carried by a blocking element movable relative to the housing between:
at least a cap insertion configuration, in which the orthogonal projections of the first area and of the second area in a transverse plane substantially perpendicular to the longitudinal axis are separated by an insertion distance, and;
a cap blocking configuration, in which the first area and the second area are located in separate transverse planes, and in which the orthogonal projections of the first area and of the second area in said transverse plane are separated by a blocking distance less than the insertion distance and adapted to block the translation of the cap relative to the removal member in a removal direction opposite to the insertion direction.

A "transverse plane" means a plane not parallel to the longitudinal axis, preferably substantially perpendicular to the longitudinal axis.

Thus, since the insertion distance is greater than the blocking distance, the passage presented to the cap during its insertion in the insertion direction is wider than the passage presented to the same cap in the blocking configuration. Due to the difference in distance, therefore, the first and second areas define, in the insertion configuration, a larger passage for the cap which is inserted in the insertion direction, since in this insertion direction, this passage is defined by the orthogonal projection of the first and second areas on the transverse plane. In other words, it is proposed to block the cap in the removal member by frictional locking of the blocking element. Thus, to block the cap in the removal member, there is no need to hook the cap behind it; there is in fact no need for the presence of a shoulder on the cap. The proposed removal member can therefore adapt to all types of injection device, irrespective of the shape, and in particular irrespective of the shape of the cap.

In addition, blocking is provided by friction of the cap by at least the first and second areas, which is more reliable than blocking provided by elastic lugs, which could accidentally become unhooked when removing the cap and which may require additional means for attachment to the cap.

Preferably, the first and second areas are arranged, in the insertion configuration, in the same longitudinal plane passing through the longitudinal axis, or in different longitudinal planes. In the blocking configuration, the first and second areas are located in separate transverse planes farther away from each other than in the insertion position. In addition, we understand that the greater the distance separating the different transverse planes containing the first and second support areas, the smaller the support distance separating their orthogonal projections in a transverse plane substantially perpendicular to the longitudinal axis. Reducing this support distance blocks, by frictional locking, the cap in the removal member.

We understand that the housing for the cap corresponds to a space left free to receive the cap in the removal member to protect the needle of the injection device in the storage position before use. The housing contour may have any shape, passing through the first and second areas. The contour may be closed or open. It may have any general geometrical shape such as a cylinder of circular cross-section or any geometrical shape. The contour may further be provided with recesses or internal projections, in particular to form support areas for the cap.

In addition, we understand that the blocking member may be attached to the rest of the removal member or made in one piece with it.

We also understand that the injection device may comprise a single injection syringe, comprising a body provided with a hollow needle and intended to administer a product by injection. The injection syringe may possibly take the shape of a cartridge to which a needle is attached. The injection device may also comprise a safety device for injection syringe, or an auto-injector device, with or without the injection syringe.

The removal member may further comprise one or more of the following characteristics, taken alone or in combination.

The housing is further defined by a third support area called third area, intended to support the cap to prevent it from pivoting relative to at least one of said first and second areas in a longitudinal plane, at least when the blocking element moves between its insertion and blocking configurations. The first, second and third support areas are arranged staggered each side of the longitudinal axis and in at least two separate transverse planes when the blocking element is in the blocking configuration.

The "first, second and third support areas being arranged staggered each side of the longitudinal axis in separate transverse planes" preferably means that the orthogonal projections of two of the first, second and third support areas in a transverse plane substantially perpendicular to the longitudinal axis are arranged on one side of the longitudinal axis while the orthogonal projection of the other of said first, second and third support areas is located on the other side of the longitudinal axis. The first, second and third support areas whose orthogonal projection is located on the other side of the longitudinal axis (relative to the orthogonal projections of the two first, second and third support areas located on the same side of the longitudinal axis) is located axially between the two first, second and third support areas located on the same side of the longitudinal axis. The sides of the longitudinal axis in which, for one the orthogonal projections of two of said first, second and third support areas are located and, for the other the orthogonal projection of the other of said first, second and third support areas is located, are separated by a longitudinal plane passing through the longitudinal axis. Preferably, the first, second and third support areas are arranged in the same longitudinal plane passing through the longitudinal axis, staggered each side of the longitudinal axis.

We understand that the third area is carried in this case by the removal member and interacts with the cap. Alternatively, other means could be used to prevent the cap from pivoting, for example by providing a third area carried by the removal member and interacting with the injection device to prevent the cap from pivoting relative to the removal member.

At least one of the first, second and third areas forms an axial guiding means for guiding the cap between the insertion configuration and the blocking configuration, for example a tubular groove arranged in a bottom of the removal member, or a boss projecting from an inner tubular wall of the removal member, or a second cap passage opening. This axial guiding means prevents the cap from pivoting relative to the first and second areas when inserting the cap in the housing.

The blocking element comprises a plate defining at least a first cap passage opening whose contour defines at least the first area, preferably the contour of the first passage opening also defines at least one of the second area and third area. Preferably, the first opening defines the second area, substantially diametrically opposite the first area. For example, the plate can be simple with a single opening or folded, with possibly several openings. When the plate is folded and comprises two openings, the second opening may define the third area. According to another embodiment, the plate may also be folded and comprise only one opening. According to this embodiment, one of the support areas will be formed by the opening, the other support areas will be carried by the removal member.

"Plate" preferably means a part whose general length and width dimensions are very large compared with the thickness. The plate may possibly comprise reliefs.

The contour of the first opening may have any shape. The contour may be closed or open. It may have a general geometrical shape such as a circle, a polygon such as a regular pentagon, or a star polygon, or any geometrical shape. The contour may further be provided with recesses or internal projections, in particular so that the support areas have a certain degree of flexibility allowing the cap to be inserted easily in the housing.

The blocking element and the removal member comprise complementary shapes or each a flat surface defining an axial stop adapted to block the translation of the blocking element relative to the removal member in the direction of removal of the cap in the removal member.

The blocking element is movable relative to the housing so as to also take a rest configuration, in which the orthogonal projections of the first area and of the second area in a transverse plane are separated by a rest distance less than the blocking distance.

We understand that the blocking element may take a rest configuration corresponding to the positions of the first and second areas before inserting the cap. This rest configuration is one in which the blocking element may or may not be elastically deformed. Note that the rest configuration may possibly coincide with the insertion configuration.

The first area and the second area are carried by the blocking element.

The blocking element is attached to the rest of the removal member by means of an elastic pivot type connection tending to return the blocking element to its blocking configuration. The pivot may be movable in translation in the removal member.

The blocking element is a plate folded so as to define two portions extending each side of an axis for pivoting the portions relative to one another. At least one of the two portions comprises a cap passage opening, and the two portions form an angle between them. The angle is different from 180°, preferably between 30° and 150°. The change in angle of the blocking element between the insertion configuration and the blocking configuration is preferably between 15° and 60°. The change in angle of the blocking element between the rest configuration and the insertion configuration is preferably between 0° and 30°.

Each of the two portions comprises a cap passage opening, as well as means for attachment to said housing, such as lugs cooperating with at least one groove provided in the housing, and preferably with two grooves provided in the housing.

Each of the two portions comprises a cap passage opening.

The plate comprises a passage opening extending over the two portions.

The axial stop is formed by complementary shapes of the plate and of the removal member such as for example lugs cooperating with at least one stopped groove provided each side of the housing in the removal member. Preferably, the lugs cooperate with two grooves provided each side of the housing in the removal member.

The removal member comprises an outer skirt allowing a user to grip the removal member. This skirt preferably has an annular or frustoconical shape, having a surface for gripping by the user, provided with gripping reliefs or a flared portion.

The blocking element comprises metal or plastic, preferably polypropylene.

The blocking element is elastically deformable between at least the insertion configuration and the blocking configuration. In other words, it moves from one configuration to the other by elastic deformation. Preferably, if it can also take a rest configuration, it is also under the effect of an elastic deformation.

The elastically deformable blocking element can be mounted in the housing by means of an embedded connection, for example by clipping or staking.

The blocking element moves from the cap insertion configuration to the cap blocking configuration under the action of a pushing element movable relative to the housing, the pushing element being separate from the cap, between a non-pressed position in which the blocking element is in the cap insertion configuration and a pressed position in which the blocking element is in the cap blocking configuration under the action of the pushing element, the pushing element being provided with locking means adapted to immobilize it relative to the housing in the pressed position.

The removal member and the blocking element each comprise a flat surface defining an axial stop, the portion of the blocking element forms a skirt provided at its distal end with a collar, and having the same longitudinal axis as the housing, the flat surface of the blocking element is included in a distal surface of the collar of the blocking element, and the flat surface of the removal member is part of a base of a movable end carrying the pushing element. Thus, the support points of the collar on the removal member are distributed over the collar, which improves the blocking of the blocking element in the removal member, thereby making the removal member more reliable.

The blocking element and the removal member comprise complementary shapes defining an angular stop adapted to block the rotation of the blocking element relative to the removal member such that the angular orientation of the blocking element relative to the pushing element allows the transition from the cap insertion configuration to the cap blocking configuration under the action of the pushing element.

The cap is a rigid needle shield (RNS) type cap, combining a flexible portion for tightness and a rigid portion to hold the cap. This type of cap is used in particular for a pre-filled injection syringe.

The orthogonal projection of the support distance between the first and second areas is strictly greater than a cap diameter Dc, preferably 0.5% greater, 1% greater, 2% greater, or more preferably 5% greater than the cap diameter Dc. The diameter Dc preferably corresponds to the diameter half-way up the cap, it may also correspond to the maximum diameter of the cap or to the diameter at the distal end of the cap. Note that in this description, the distal direction designates the direction closest to the skin of a patient at the time of an injection, and the proximal direction designates the opposite direction. In other words, we could say that the distal direction is that going towards the front of the injection device. In particular, the distal end of a part corresponds to the end located on the side of the injection needle and the proximal end corresponds to the opposite end.

The removal member comprises at least one flat end complementary to at least one flat stop of a distal end of the injection device, the flat end and the flat stop being adapted to cooperate together so as to block in translation the removal member on the distal end of the injection device. Thus, the removal member is held blocked axially on the injection device.

The flat end and the flat stop are positioned so that a rotation of the removal member relative to the sleeve disengages the flat stops from the flat ends. Consequently, the removal member can be removed axially from the distal end of the injection device, so as to control the removal of the removal member.

The removal member comprises a shape complementary to a shape of a distal end of the injection device, the two shapes being adapted to cooperate together so as to block in rotation the removal member (317) on the distal end (311) of the injection device. Due to the cooperation of the two complementary shapes, the removal member is positioned angularly on the distal end, and held in this position. Consequently, to remove the removal member, in order to remove the protective cap, the removal member must be rotated through a certain angle relative to the distal end of the injection device, so as to control the removal of the removal member, and therefore of the protective cap. Thus, when the injection device comprises an auto-injector device, and if the latter is dropped, the removal member and the auto-injector device are prevented from separating, and the auto-injector device is prevented from being accidentally activated, which is particularly advantageous. Advantageously, the injection device comprises an auto-injector device.

The removal member comprises circular arc-shaped elements intended to cooperate with trapezoidal recesses of an outer box of an auto-injector included in an injection device so as to allow the removal member to be translated by rotation on the outer box. The slope of the recess of the outer box facilitates the translation of the removal member by rotation and the release of the circular arc-shaped element. This therefore facilitates removal of the removal member from the injection device, and therefore removal of the protective cap.

The invention also relates to an injection device comprising a removal member as described above.

Preferably, the injection device comprises a safety device to protect the user from being pricked by the needle after use.

The invention also relates to a method for assembling a removal member on an injection device comprising a needle and a removable needle protective cap. The removal device comprises a housing having a longitudinal axis and being adapted to receive the cap along an insertion direction. The housing is defined by at least first and second support areas called first and second areas intended to support the cap housed in the housing, the first area being carried by a blocking element movable relative to the housing. The method comprises at least the following steps:

inserting the cap opposite the housing, in the insertion direction, the blocking element being in a cap insertion configuration, in which the first area and the second area are arranged such that their orthogonal projections in a transverse plane substantially perpendicular to the longitudinal axis are separated by an insertion distance;

stopping the insertion of the cap in the removal member, the blocking element takes a cap blocking configuration, in which the first area and the second area are located in separate transverse planes, and arranged such that their orthogonal projections in said transverse plane are separated by a blocking distance less than the insertion distance and adapted to block the translation of the cap relative to the removal member in a removal direction opposite to the cap insertion direction.

The cap can be inserted opposite the housing such that the cap exerts a pressure on the blocking element to move from a rest configuration in which the orthogonal projections of the first area and of the second area in a transverse plane are separated by a rest distance less than the blocking distance to an insertion configuration and to increase the distance separating said orthogonal projections, up to the insertion distance.

The blocking element can be moved from the cap insertion configuration to the cap blocking configuration by moving the first area relative to second area by means of a pushing element which is moved relative to the housing between a non-pressed position in which the blocking element is in the cap insertion configuration and a pressed position in which the blocking element is in the cap blocking configuration, and the pushing element is blocked relative to the housing in the pressed position.

The invention also relates to a method for using a removal member assembled according to an assembly method as described above, during which a user presses the movable end of the removal member, mounted movable by the user relative to a surface for gripping the removal member, between a non-pressed position and a pressed position in which the blocking element is in the cap blocking configuration under the action of a pushing element.

BRIEF DESCRIPTION OF THE DRAWINGS

Several embodiments of the invention, given as non-limiting examples, are described below referring to the attached figures in which:

FIGS. 3A, 3B, 3C are diagrammatic cross-sectional side views of a removal member according to three modes of connection between the blocking element and the removal member: an elastic pivot connection (FIG. 3A), an elastic movable pivot connection (FIG. 3B), an embedded connection (FIG. 3C).

FIGS. 1A-C and 2A-C comprise in the upper section a diagrammatic side view of the blocking element, in the upper middle section a diagrammatic plan view of the blocking element, in the lower middle section a diagrammatic side view of the blocking element and the cap, in the lower section a diagrammatic view of the contour of the cap and the contour of the blocking element passage opening.

FIGS. 3A-C illustrate the blocking element in the insertion position with a solid line and in the blocking configuration with a thin dashed line. The elastic feature of the connections and embedded connection is symbolized by a schematized spring.

Figure 6:
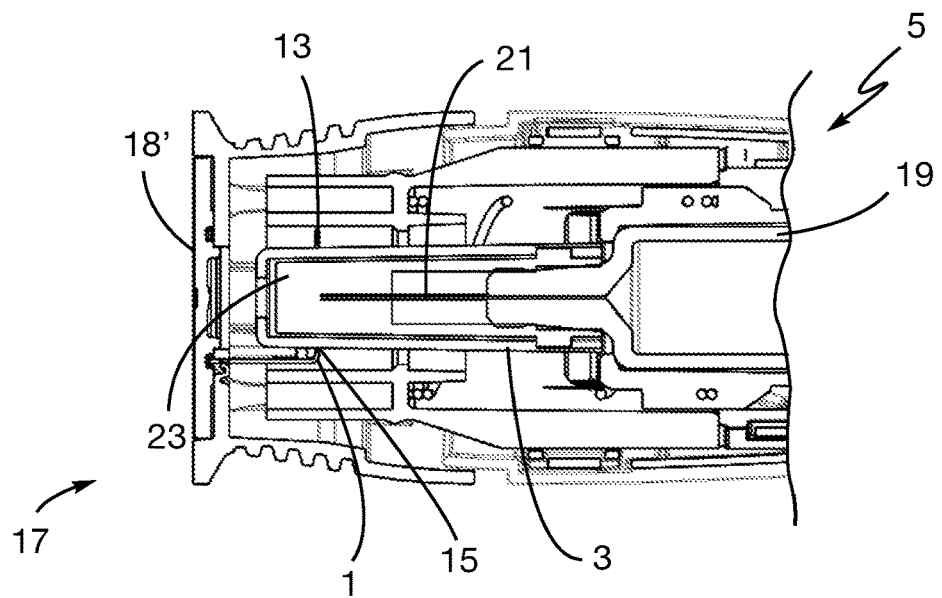
Figure 7:
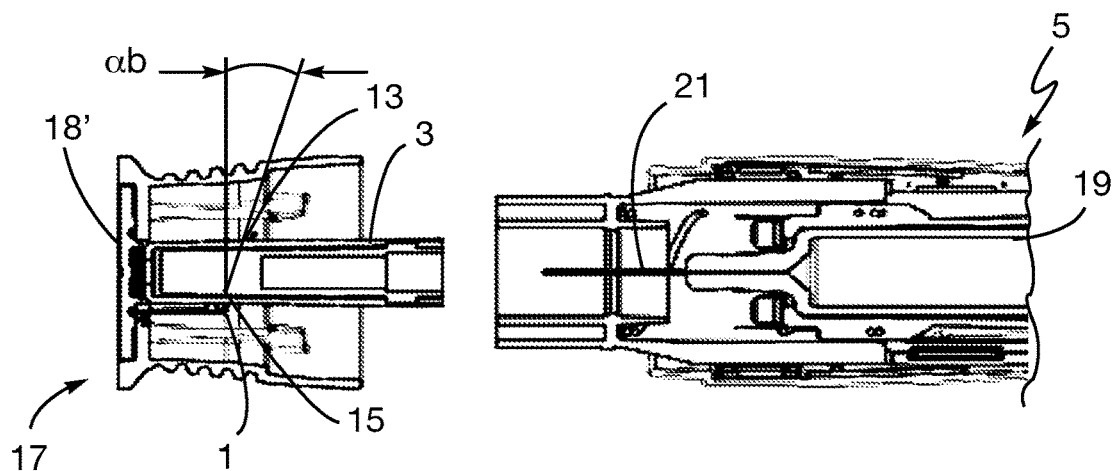

A first embodiment of the first operating principle of the invention is illustrated on FIGS. 4A to 7 in which:

FIGS. 4A and 4B are perspective views of a movable end of the removal member according to two alternative embodiments;

FIGS. 5A and 5B are perspective views of the blocking element according to two alternative embodiments;

FIG. 6 is a longitudinal cross-sectional view of the assembly of the removal member on the injection device, the blocking element of the removal member being in the insertion configuration;

FIG. 7 is a longitudinal cross-sectional view of the assembly of the removal member and the injection device, after removing the cap.

Figure 8:
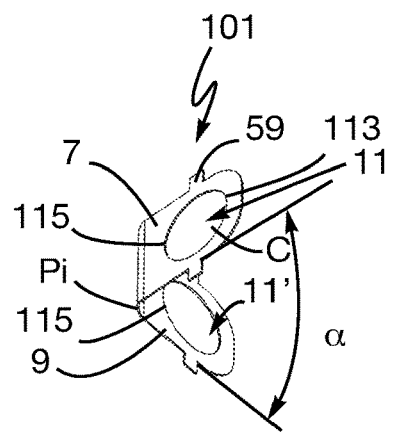
Figure 9:
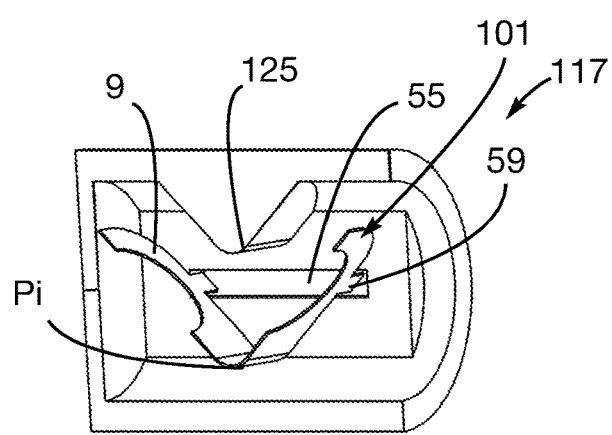
Figure 10:
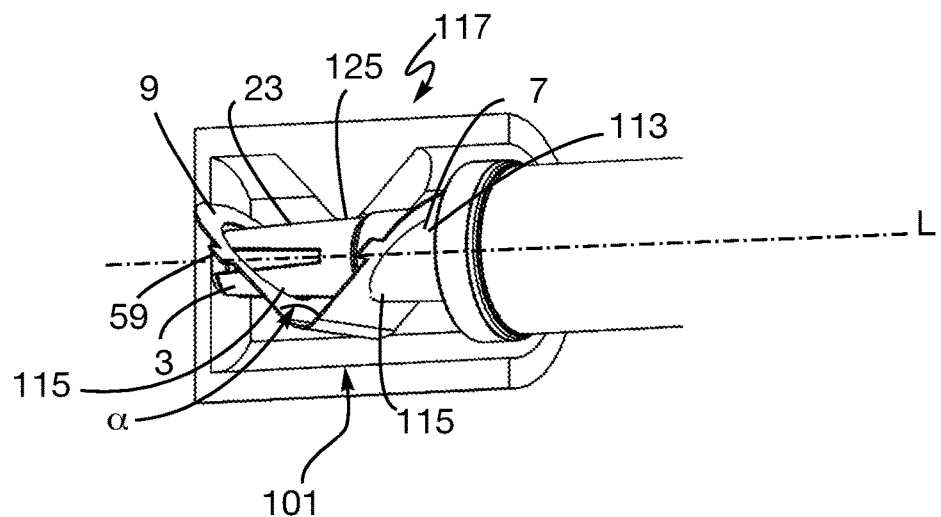
Figure 11:
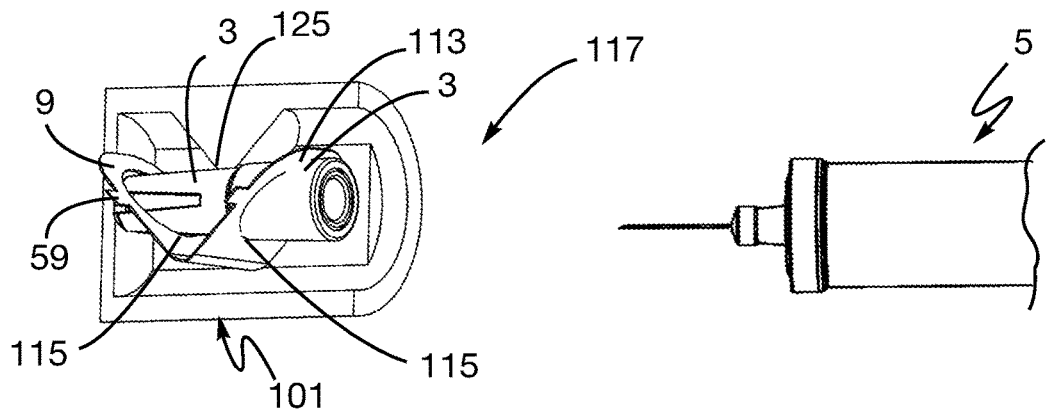

A second embodiment of the first operating principle of the invention is illustrated on FIGS. 8 to 12D in which:

FIG. 8 is a perspective view of the blocking element shown not assembled in the removal member;

FIG. 9 is a perspective longitudinal cross-sectional view of the removal member before assembly on an injection device;

FIG. 10 is a perspective longitudinal cross-sectional view of the removal member assembled on an injection device;

FIG. 11 is a perspective longitudinal cross-sectional view of the removal member shown after removing the cap from the injection device;

FIGS. 12A to 12D show various alternatives of a blocking element of a removal member as shown on FIGS. 8 to 11.

Figure 17:
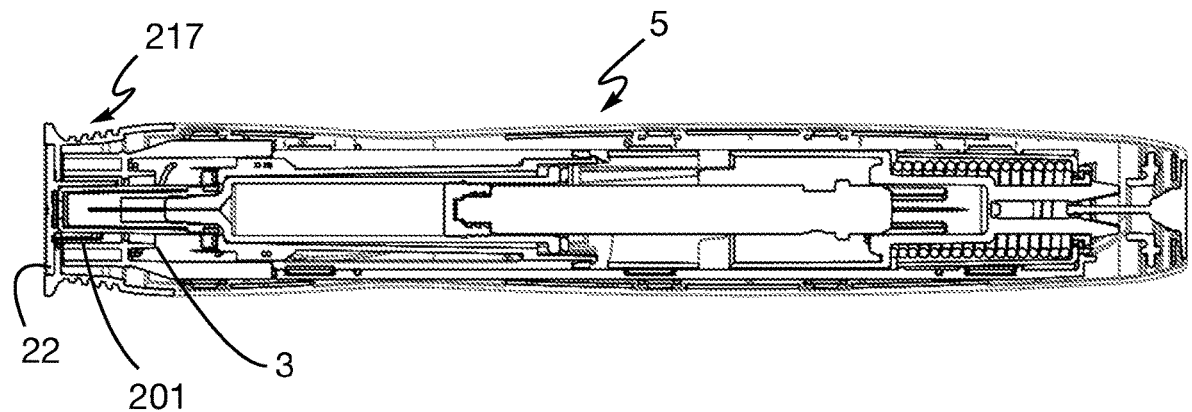
Figure 18:
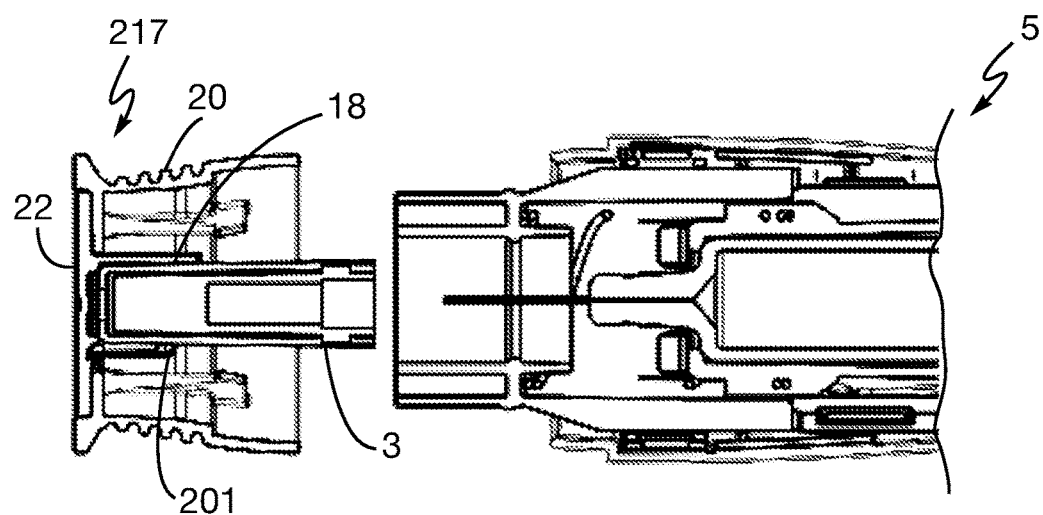

A first embodiment of the second operating principle of the invention is illustrated on FIGS. 13 to 18 in which:

FIG. 13 is a perspective view from above of a pushing element of the removal member;

FIG. 14 is a perspective cross-sectional view of a removal member with the pushing element in the non-pressed position;

FIGS. 15 to 18 are longitudinal cross-sectional views of the removal member and of the injection device in which:

FIG. 15 illustrates the removal member as pre-assembled on the injection device;

FIGS. 16 and 17 illustrate the removal member as assembled to the injection device and in the blocking configuration, FIG. 16 being a partial enlarged view of FIG. 17;

FIG. 18 illustrates the removal member and the cap being removed from the injection device.

Figure 19:
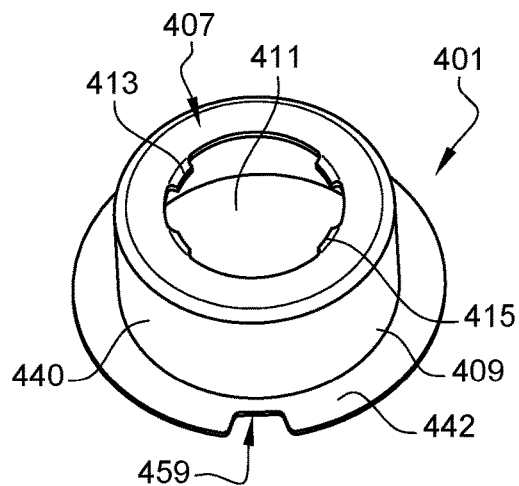
Figure 20:
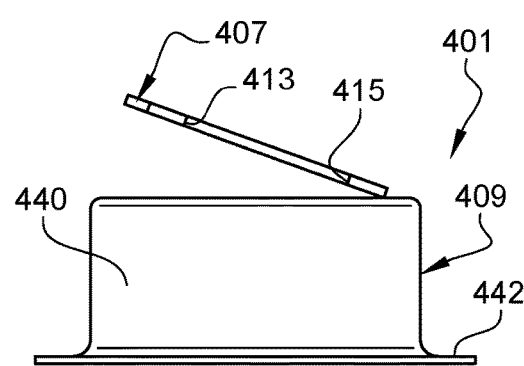
Figure 21:
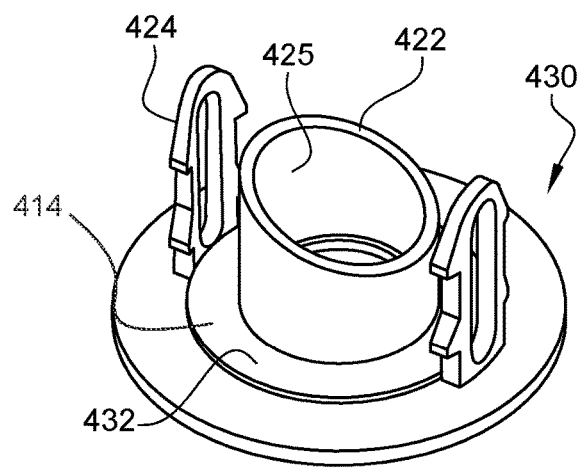
Figure 22:
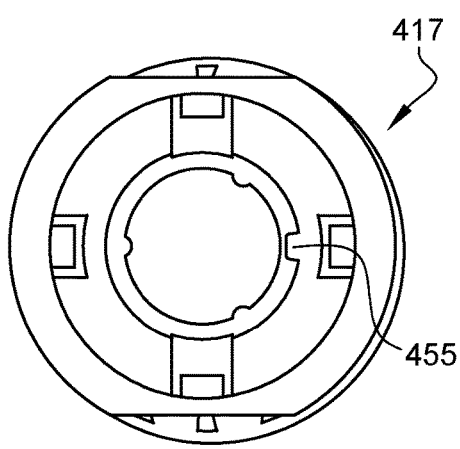
Figure 23:
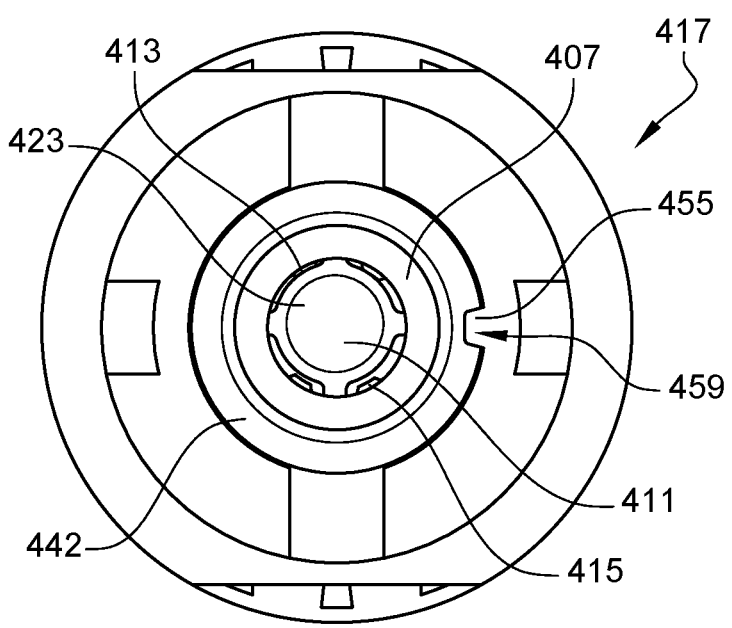

A second embodiment of the second operating principle of the invention is illustrated on FIGS. 19 to 23 in which:

FIG. 19 is a perspective view from above of the blocking element;

FIG. 20 is a side view of the blocking element;

FIG. 21 is a perspective view from above of a movable end of the removal member;

FIG. 22 is a perspective view from below of a removal member not assembled with the movable end and the blocking element;

FIG. 23 is a perspective view from below of the removal member in which the blocking element is assembled.

Figure 24:
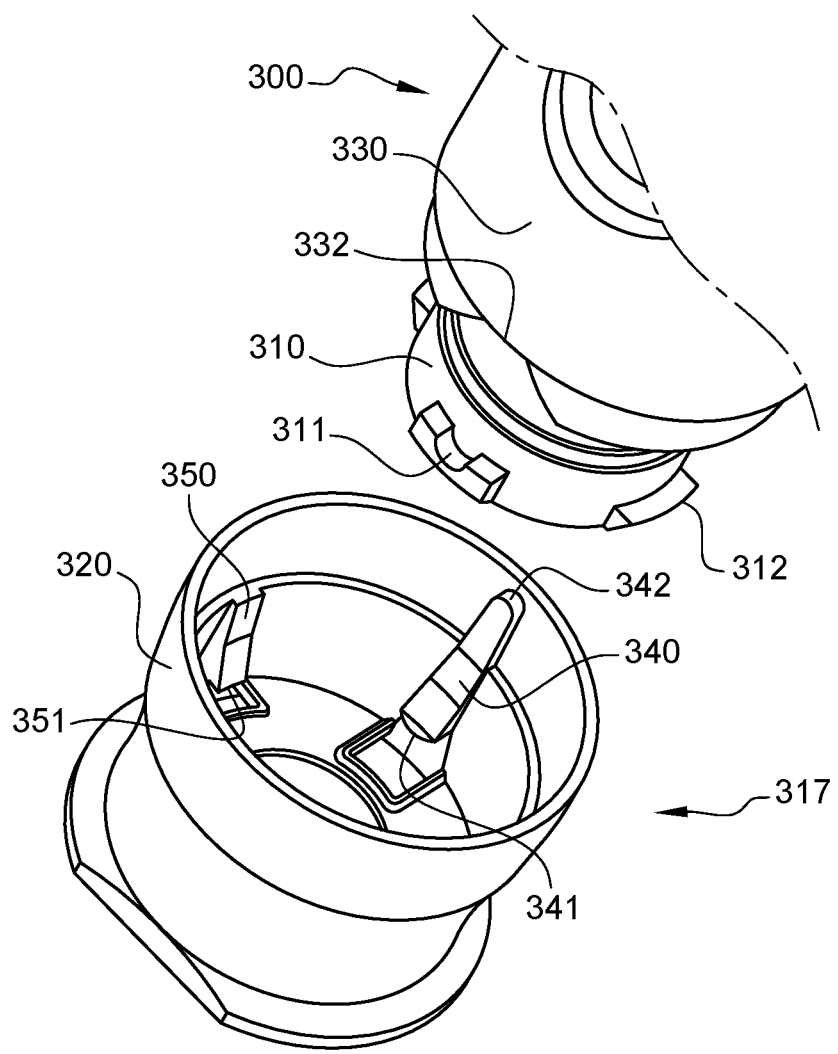

Two special embodiments, compatible with the two operating principles, are illustrated on FIG. 24, on which the entire removal member and part of an injection device are shown in perspective.

DETAILED DESCRIPTION OF THE INVENTION

Referring to FIGS. 1A-C, 2A-C, 3A-C, the removal member 17, 117, 217 according to the invention comprises a housing 23 adapted to receive a needle protective cap 3. The housing 23 has a longitudinal axis L. The housing 23 is defined by first 13, 113, 213, second 15, 115, 215 and third 25, 125, 225 support areas of the cap 3 intended to support the cap 3 and block it in the removal member 17, 117, 217. The removal member 17, 117, 217 comprises a blocking element 1, 101, 201 carrying the first support area 13, 113, 213 and movable relative to the housing 23 between:

a cap 3 insertion configuration (FIGS. 1B, 2A and solid lines on FIGS. 3A-C) in which the orthogonal projections of the first area 13, 113, 213 and of the second area 15, 115, 215 in a transverse plane substantially perpendicular to the longitudinal axis L are separated by an insertion distance Di allowing the cap 3 to be inserted in the removal member 1, 101, 201, and a blocking configuration (FIGS. 1C, 2C and thin dashed lines of FIGS. 3A-C), in which the first area 13, 113, 213 and the second area 15, 115, 215 are located in separate transverse planes, and in which the orthogonal projections of the first area 13, 113, 213 and of the second area 15, 115, 215 in said transverse plane are separated by a blocking distance Db less than the insertion distance Di and adapted to block the translation of the cap 3 relative to the removal member 17, 117, 217 in a removal direction opposite to the insertion direction, in which removal of the cap 3 relative to the removal member 1, 101, 201 is prevented.

The third area 25, 125, 225 is intended to prevent the cap 3 from pivoting relative to at least one of the first 13, 113, 213 and second 15, 115, 215 areas in a longitudinal plane, passing through the longitudinal axis, at least when the blocking element 1, 101, 201 moves between its insertion and blocking configurations. The first 13, 113, 213, second 15, 115, 215 and third 25, 125, 225 areas are arranged staggered each side of the longitudinal axis L and in at least two separate transverse planes when the blocking element 1, 101, 201 is in the blocking configuration.

In the blocking configuration, the cap 3 is blocked by frictional locking between the first 13, 113, 213, second 15, 115, 215 and third 25, 125, 225 areas. In the embodiments illustrated, the blocking element 1, 101, 201 takes the shape of a plate provided with a passage opening 11 defining at least the first area 13, 113, 213. The blocking element 1, 101, 201 may take any other suitable shape.

The removal member 17, 117, 217 comprises at least one axial stop 14, 114, 214 limiting the displacement of the blocking element 1, 101, 201 relative to the removal member 17, 117, 217, and adapted to block the translation of the blocking element 1, 101, 201 relative to the removal member 17, 117, 217 in the direction of removal of the cap 3 in the removal member 17, 117, 217. This axial stop 14, 114, 214 may consist of a shoulder 14, 114, 214 against which the end 30, 130, 230 of the blocking element 1, 101, 201, opposite to an elastic pivot connection P1, P3 (FIGS. 3A and 3B), or to an elastic embedded connection P2 thereof (FIG. 3C), is resting. The axial stop 14, 114, 214 and the end 30, 130, 230 comprise complementary shapes. The axial stop may also consist of an embedded connection of the blocking element 1, 101, 201 in the removal member 17, 117, 217, a pivot connection or any other suitable means.

Figure 1A:
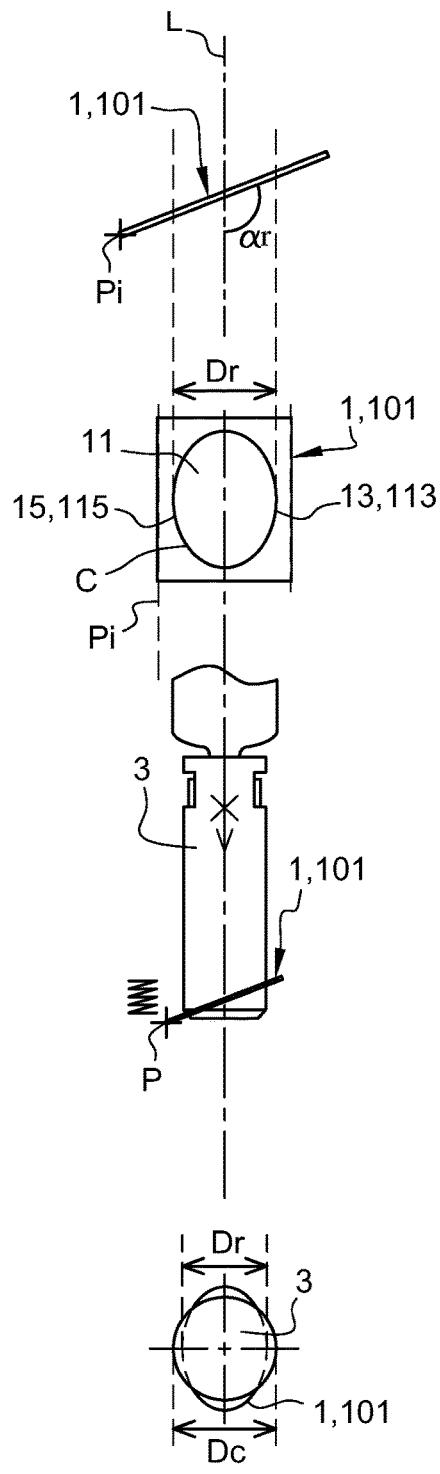
FIGS. 1A, 1B, 1C are diagrammatic views of a first operating principle of the invention in which the blocking element is elastically deformable between a rest configuration (FIG. 1A), an insertion configuration (FIG. 1B) and a blocking configuration (FIG. 1C)

According to a first operating principle of the invention, and referring to FIGS. 1A-C, 3A, 3B, 3C, the blocking element 1, 101 is elastically deformable between the cap 3 insertion configuration and the cap 3 blocking configuration. The elastic deformation may be provided by means of an elastic pivot connection P1 of the blocking element 101 (FIG. 3B), an elastic embedded connection P2 of the blocking element 1 (FIG. 3C) or by the elasticity of the blocking element itself (FIGS. 9 to 12D). According to this first operating principle, the cap 3 and the blocking element 1, 101 are chosen such that:

a) In the rest configuration of the blocking element 1, 101 illustrated on FIG. 1A:
the blocking element 1, 101 forms a rest angle $\alpha r$ with the longitudinal axis L;
the rest distance Dr separating the orthogonal projections of the first area 13, 113 and of the second area 15, 115 is less than the diameter Dc of the cap 3 in the portion of the cap 3 arranged at the same height as the first 13, 113 and second 15, 115 areas.

Figure 1B:
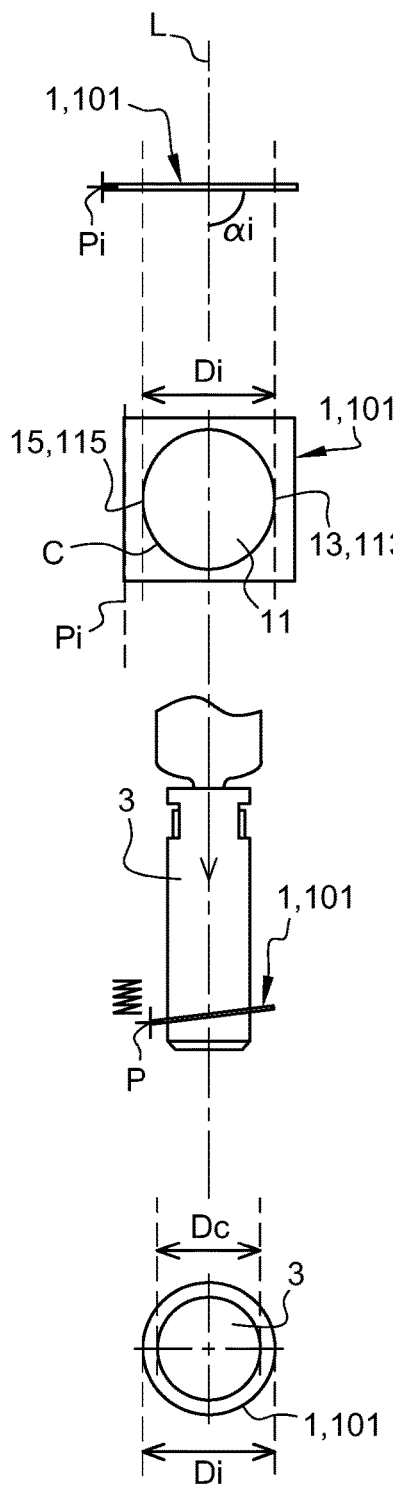

In this rest configuration, the cap 3 cannot pass through the passage opening 11, which is schematised by the crossed arrow on FIG. 1A. The pressure of the cap 3 on the blocking element 1, 101 elastically deforms the blocking element 1, 101 towards its insertion configuration.

b) In the insertion configuration in which the cap 3 is inserted in the blocking element 1, 101 illustrated on FIG. 1B:
the blocking element 1, 101 forms an insertion angle $\alpha i$ with the longitudinal axis L, the insertion angle $\alpha i$ being less than the rest angle $\alpha r$;
the insertion distance Di separating the orthogonal projections of the first area 13, 113 and of the second area 15, 115 is greater than the rest distance Dr and greater than the diameter Dc of the cap 3 in the portion of the cap 3 arranged at the same height as the first area 13, 113 and the second area 15, 115.

Figure 1C:
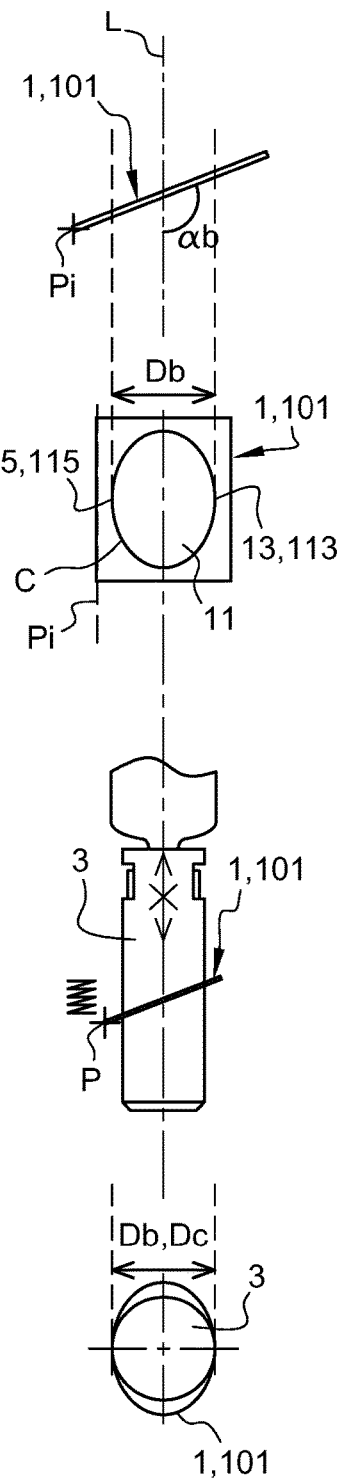

In this insertion configuration, the cap 3 can pass through the passage opening 11, which is schematised by the non-crossed arrow on FIG. 1B. The blocking element 1, 101 tends to elastically deform towards its blocking configuration.

c) In the blocking configuration in which the cap 3 is blocked in the blocking element 1, 101 illustrated on FIG. 1C:
the blocking element 1, 101 forms a blocking angle $\alpha b$ with the longitudinal axis L, the blocking angle $\alpha b$ being greater than the insertion angle $\alpha i$ and less than the rest angle $\alpha r$;
the blocking distance Db separating the orthogonal projections of the first area 13, 113 and of the second area 15, 115 is greater than the rest distance Dr, less than the insertion distance Di and is equal to the diameter Dc of the cap 3 in the portion of the cap 3 arranged at the same height as the first area 13, 113 and the second area 15, 115, tending, due to the elasticity of the blocking element, 1, 101, to be less than this diameter Dc of the cap 3.

In this blocking configuration, the cap 3 is blocked in the passage opening 11, it cannot move forward any further through the passage opening, either because it is resting against the bottom of the removal member, or because the injection device 5 is resting on the removal member. Similarly, the cap 3 cannot move backward, since it is held in the blocking element 1, 101 and since the blocking element 1, 101 is held in the cap 3. This double blocking is schematised by the crossed double arrow on FIG. 1C. The blocking element 1, 101 tends to elastically deform towards its rest configuration, thus keeping the cap blocked in the passage opening 11.

Figure 2A:
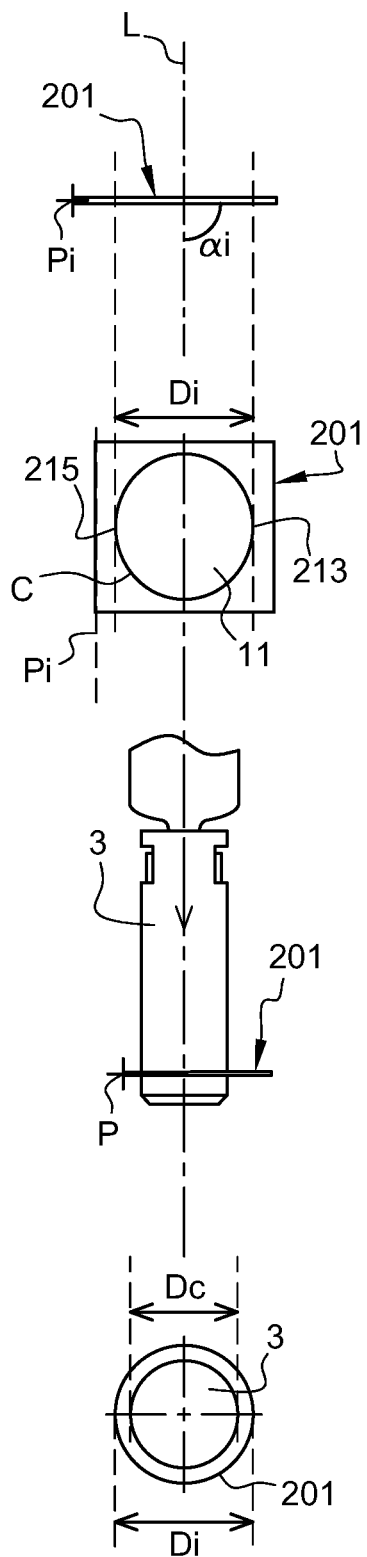
FIGS. 2A, 2B, 2C are diagrammatic views of a second operating principle of the invention in which the blocking element is deformed by means of a pushing element between a rest configuration (FIG. 2A) and a blocking configuration (FIG. 2C), going via an intermediate configuration (FIG. 2B)
Figure 2B:
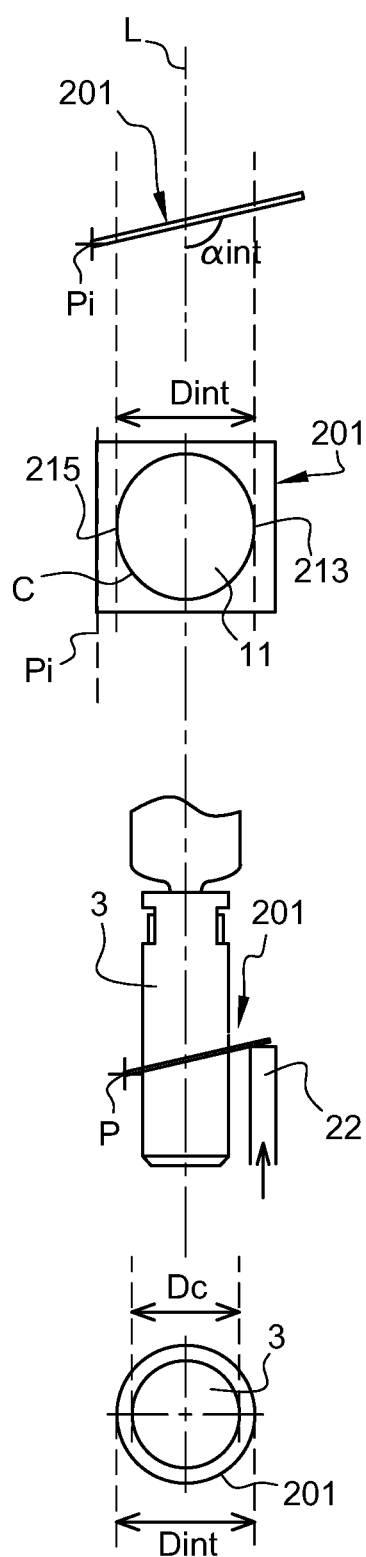

According to a second operating principle of the invention, and referring to FIGS. 2A-C and 3A, the blocking element 201 is moved and/or deformed about a pivoting point Pi by a pushing element 22 between an insertion configuration (FIG. 2A) and a blocking configuration (FIG. 2C), going via an intermediate configuration (FIG. 2B).

According to this second operating principle, the cap 3 and the blocking element 201 are chosen such that:

a) In the insertion configuration in which the cap 3 is inserted in the blocking element 201 illustrated on FIG. 2A:
the blocking element 201 forms an insertion angle $\alpha i$ with the longitudinal axis L;
the insertion distance Di separating the orthogonal projections of the first area 213 and of the second area 215 is greater than the diameter Dc of the cap 3 in the portion of the cap 3 arranged at the same height as the first area 213 and the second area 215.

In this insertion configuration, the cap 3 can pass through the passage opening 11, which is schematised by the non-crossed arrow on FIG. 2A.

Figure 2C:
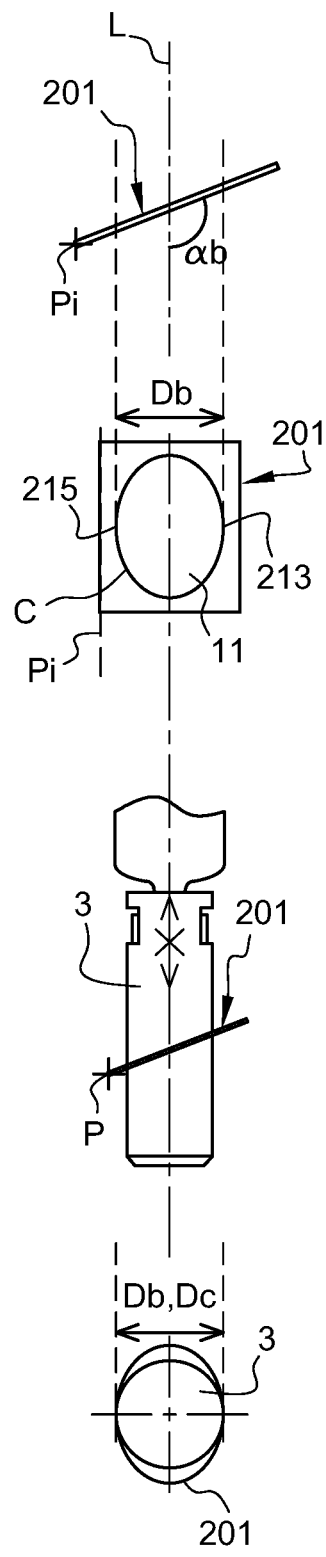

Once the cap 3 has been inserted in the passage opening 11, the blocking element 201 can be deformed by the pushing element 22 moved longitudinally. This movement is symbolised by the arrow shown on FIG. 2B until the blocking element 201 is in its blocking configuration.

b) In the blocking configuration in which the cap 3 is blocked in the blocking element 201 illustrated on FIG. 2C:
the blocking element 201 forms a blocking angle $\alpha b$ with the longitudinal axis L, the blocking angle $\alpha b$ being greater than the insertion angle $\alpha i$ and than an intermediate angle αint formed by the blocking element 201 between its rest and blocking configurations;

the rest distance Dr separating the orthogonal projections of the first area 213 and of the second area 215 is less than the insertion distance Di and is equal to the diameter Dc of the cap 3 in the portion of the cap 3 arranged at the same height as the first area 213 and the second area 215.

In this blocking configuration, the cap 3 is blocked in the passage opening 11, it cannot move forward any further through the passage opening or move backward, which is schematised by the double crossed arrow on FIG. 1C. The pushing element 22 moves the blocking element 201 until it deforms it elastically or permanently to guarantee that the cap 3 is held.

As shown on FIGS. 3A-C, the third area 25, 125, 225 is intended to support the cap 3 to prevent it from pivoting relative to at least one of the first area 13, 113, 213 and a second area 15, 115, 215 in a longitudinal plane. The first 13, 113, 213, second 15, 115, 215 and third 25, 125, 225 areas are arranged staggered each side of the longitudinal axis L. The first 13, 113, 213, second 15, 115, 215 and third 25, 125, 225 areas are located in separate transverse planes when the blocking element 1, 101, 201 is in the blocking configuration. The third area 25, 125, 225 forms an axial guiding means for guiding the cap 3 between the insertion configuration and the blocking configuration.

According to a first operating principle and a first embodiment, as shown on FIGS. 4A to 7 and 1A-C, the removal member 17 comprises a blocking element 1 taking the shape of a plate folded so as to define two portions 7 and 9 extending each side of a folding radius defining a pivoting axis Pi of the portions 7 and 9 relative to one another. The blocking element 1 and the removal member 17 comprise complementary shapes 29, 31 defining an axial stop adapted to block the translation of the blocking element 1 relative to the removal member 17 in the direction of removal of the cap 3 in the removal member 17. The two portions 7 and 9 form an angle α between each other, a rest angle αr close to 135° in the rest configuration, an insertion angle αi of 120° in the insertion configuration and a blocking angle αb of 135° in the blocking configuration, being nevertheless slightly less than the rest angle αr. As shown, the portion 7 comprises a cap 3 passage opening 11. In this embodiment, the blocking element 1 comprises a folded plate defining the two portions 7 and 9. As described below, the blocking element 1 can be elastically or permanently deformed, for example about a pivoting axis Pi. The contour C of the passage opening 11 defines a first cap 3 support area 13, called "first area" 13. It also defines a second cap 3 support area 15, called "second area" 15. In this embodiment, the first area 13 and the second area 15 are carried by the blocking element 1. In this embodiment, the third area, not shown, consists of the injection device 5 resting on the removal member 17.

The housing 23 has a longitudinal axis L, which coincides with the longitudinal axis L of the cap 3 when the cap is in the housing 23. The first and second areas 13 and 15 are arranged each side of the longitudinal axis L and located in separate transverse planes when the blocking element 1 is in the blocking configuration, as shown on FIG. 7, and on the top view of FIG. 1C.

In another embodiment, not shown, the second area can be carried by the removal member, the third area can be carried by the blocking element.

The blocking element 1 is movable between the cap 3 insertion configuration (FIGS. 1B and 6) and the cap 3 blocking configuration (FIGS. 10 and 7). In this case, the portion 9 is a portion for attaching the blocking element 1 on the rest of the removal member 17 (described below) by means of an embedded connection, more precisely by clipping or staking. Thus, after removing the cap 3 by means of the blocking element 1, the blocking element 1 is attached to the removal member 17, thus blocking the cap 3 in the removal member 17. The blocking element 1 and a movable end 18' of the removal member 17 comprise complementary shapes 29 and 31 adapted to cooperate to form an embedded type connection. This connection is adapted to block the translation of the blocking element 1 relative to the removal member 17 in a removal direction opposite to the direction of insertion of the cap 3 in the removal member 17.

In an alternative embodiment, not shown, the blocking element comprises a simple plate provided with the passage opening and whose outer edge is attached by an embedded type connection to the rest of a removal member. In this other embodiment, the contour of the opening opposite the embedded edge of the plate forms the first support area.

The injection device 5 shown on FIGS. 6 and 7 comprises an injection syringe which comprises a body 19 provided with a hollow needle 21. The injection device 5 is intended to administer a product by injection. The removal member 17 of this embodiment comprises a housing 23 for the cap 3. The housing 23 is defined by at least the first and second areas 13 and 15. The housing 23 corresponds to the space left free to receive the cap 3 in the removal member 17, in this case it has a generally cylindrical shape, provided with projections and recesses.

According to the first operating principle and a second embodiment, as shown on FIGS. 8 to 12D, the removal member 117 comprises a blocking element 101 taking the shape of a folded plate defining the two portions 7 and 9 substantially symmetrical to one another and elastically or permanently deformable relative to one another. The two portions 7 and 9 extend each side of a folding radius defining a pivoting axis Pi. The two portions 7 and 9 form an angle α between each other, in the rest configuration a rest angle αr close to 90°. The portion 7 is crossed by a passage opening 11 defining a first cap 3 support area 113, called the "first area" 113, and a second support area 115 called the "second area". The first 113 and second 115 areas are arranged each side of the longitudinal axis L of the housing 23. The portion 9 is crossed by a passage opening 11'. In this embodiment, the first area 113 and the second area 115 are carried by the blocking element 101.

The removal member 117 comprises a boss projecting from the inner wall of the housing 23 and defining the third area 125. This third area 125 also forms an axial guiding means for guiding the cap 3 between the insertion configuration and the blocking configuration.

The blocking element 101 and the removal member 117 comprise complementary shapes: grooves 55 of the removal member 117 which stop before the proximal end of the removal member 117 and lugs 59 on the blocking element 101. The stopped grooves 55 and the lugs 59 define an axial stop adapted to block the translation of the blocking element 101 relative to the removal member 117 in the direction of removal of the cap 3 in the removal member 117.

Thus, each of the two portions 7, 9 comprises respectively a first passage opening 11 and a second passage opening 11', as well as lugs 59 cooperating with two grooves 55 of the housing 23.

In this embodiment, the mobility of the first and second areas 113, 115 is similar to an elastic movable pivot type connection tending to return the blocking element 101 to its blocking configuration. Thus, the blocking element 101 is elastically deformable. The pivot is movable in translation in the removal member 117 due to the cooperation between the grooves 55 and the lugs 59.

The removal member 117 comprises a surface for gripping the removal member 117 which is an outer skirt allowing a user to grip the removal member 117.

The injection device 5 comprises a safety device (not shown) to protect the user from being pricked by the needle after use, or an auto-injector device.

Figures 12A, 12B, 12C, 12D:
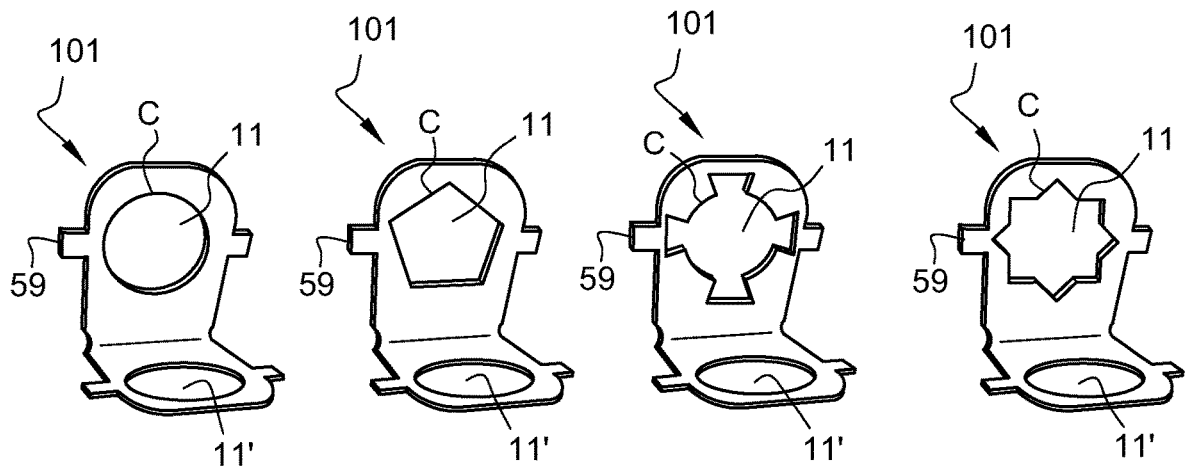

As illustrated, the contour C of the passage opening 11 may have a circular shape on FIG. 12A, the shape of a pentagon on FIG. 12B, a circular shape provided with inner projections on FIG. 12C, the shape of an 8-branch star on FIG. 12D.

For the first operating principle, assembling the removal member 17, 117 on the injection device 5 comprises the following steps.

Inserting the cap 3 opposite the housing 23, in the insertion direction for example until it abuts against the bottom of the removal member 17, 117.

Inserting the cap 3 so as to exert a pressure on the blocking element 1, 101 to make it move from a rest configuration to an insertion configuration and to increase the distance separating the orthogonal projections up to the insertion distance Di.

Stopping the insertion of the cap 3 in the removal member 17, 117. The blocking element 1, 101 moves to a blocking configuration in which the distance separating the orthogonal projections of the first area 13, 113 and of the second area 15, 115 in a transverse plane decreases to reach a distance called blocking distance Db, and to block the cap 3 in the removal member 17, 117.

According to the second operating principle, first embodiment, as shown on FIGS. 13 to 18, the removal member 217 comprises a pushing element 22 movable relative to the surface 20 for gripping the removal member 217, when assembling the removal member 217 to the injection device 5, between a non-pressed position and a pressed position.

The pushing element 22 comprises a pushing lug 18 adapted to push the blocking element 201 towards its cap 3 blocking configuration when the pushing element 22 moves from its non-pressed position to its pressed position. The pushing element 22 comprises a locking member for attachment to the removal member 217, for example attachment lugs 24 (shown on FIG. 13), adapted to be housed by elastic deformation in a groove provided in the removal member 217, the notches provided on the attachment lugs 24 making the attachment of the pushing element 22 to the removal member 217 in its pressed position more reliable. The pushing element 22 is therefore provided with locking member adapted to immobilize it relative to the housing 23 in the pressed position. In the non-pressed position, the pushing element 22 can be pre-assembled to the removal member 217 in a non-pressed pre-assembled position, without however the pushing lug 18 pushing the blocking element 201 towards its blocking configuration. Thus, the attachment lugs 24 may comprise intermediate notches to hold the pushing element 22 in this non-pressed pre-assembled configuration. The removal member 217 has an end provided with windows crossed by the pushing lug 18 and the attachment lugs 24 of the pushing element 22 in the non-pressed pre-assembled and assembled position. The pushing element 22 therefore abuts axially against the removal member 217.

FIGS. 19 to 23 illustrate a second embodiment of the second operating principle of the invention, in which the removal member 417 comprises a gripping surface (not shown on the perspective views from below), a movable end 430 and a blocking element 401. The blocking element 401 takes the shape of a plate folded so as to define two portions 407 and 409 extending each side of a folding radius defining an axis for pivoting the portions 407 and 409 relative to one another. The portion 407 is provided with a passage opening 411 defining the first and second support areas 413 and 415 which define a housing 423 of the removal member 417 adapted to receive the needle protective cap. The portion 409 forms a skirt 440 provided at its distal end with a collar 442. The movable end 430 comprises lugs 424 for attachment to the removal member 417, a truncated cylinder which forms a pushing element 422 movable relative to the surface for gripping the removal member 417, and a base 432. The truncated cylinder 422 is substantially at the center of the base 432. The truncated cylinder 422, the blocking element 401 and the cap 3 are intended to be positioned so as to have the same longitudinal axis (L) as the housing 423. The attachment lugs 424 of the movable end 430 form means for locking the pushing element 422 which are adapted to immobilize it relative to the housing 423 in the pressed position. The base 432 forms a seat for the collar 442 of the blocking element 401. The inner diameter of the collar 442 of the blocking element 401 is greater than the outer diameter of the truncated cylinder 422 of the movable end 430. The base 432 comprises a flat surface defining an axial stop 414 for the distal surface of the collar 442, which is also a flat surface. The axial stop 414 is adapted to block the translation of the blocking element 401 relative to the removal member 417 in the direction of removal of the cap in the removal member 417. In this embodiment, the support points are distributed on the collar 442, which improves the blocking of the blocking element 401 in the removal member 417. This makes the removal member reliable.

In addition, the collar 442 of the blocking element 401 comprises a notch 459 and the removal member 417 comprises a boss 455. The notch 459 of the blocking element 401 and the boss 455 of the removal member 417 are two complementary shapes defining an angular stop adapted to block the rotation of the blocking element 401 relative to the removal member 417, such that the angular orientation of the blocking element 401 relative to the pushing element 422 allows the cap 3 to move from the insertion configuration to the blocking configuration under the action of the pushing element 422. In another embodiment, not shown, the boss is carried by the collar and the notch is carried by the removal member.

The pushing element 422 carries the third support area 425. This area is intended to support the cap to prevent it from pivoting relative to the first 413 and second 415 areas in a longitudinal plane, at least when the blocking element moves between its insertion and blocking configurations. The first 413, second 415 and third 425 areas are arranged staggered each side of the longitudinal axis and in at least two separate transverse planes when the blocking element 401 is in the blocking configuration. The three support areas 413, 415 and 425 define the housing 423 for the needle protective cap, not shown here. In the blocking configuration, the first area 413 and the second area 415 are located in separate transverse planes farther away from each other than in the insertion configuration. The passage presented to the cap during its insertion is wider than the passage presented to the cap in the blocking configuration, thereby blocking the cap in the removal member 417 by frictional locking of the blocking element 401.

For the second operating principle, assembling the removal member 217, 417 on the injection device 5 comprises the following steps.

Inserting the cap 3 opposite the housing 23, 423, in the insertion direction.

Pressing the pushing element 22, 422 in the longitudinal direction relative to the surface 20 for gripping the removal member 17, 417, between a non-pressed position and a pressed position in which the blocking element 201, 401 is in the cap 3 blocking configuration under the action of the pushing element 22, 422.

In the second embodiment of the second operating principle, before inserting the cap 3, the complementary shapes 459, 455 of the blocking element 401 and of the removal member 417 are positioned so as to block in rotation the blocking element 401 relative to the removal member 417.

In a special embodiment produced according to the first or second operating principle, and shown on FIG. 24, the removal member is intended to equip an injection device comprising an auto-injector device. The auto-injector device 300 comprises an end sleeve 310, intended to be in contact with the skin of a user during the injection. The end sleeve 310, which forms the distal end of the injection device, is attached to the distal end of a syringe support (not shown), itself configured to house an injection syringe. It is also equipped with an outer box 330, whose distal end is shown here. In this embodiment, the removal member 317 comprises a gripping surface 320. The removal member 317 further comprises two ribs 340 projecting from the inner wall of the removal member 317. These ribs 340 of the removal member 317 and the end sleeve 310 have complementary shapes 341 and 311 adapted to cooperate to block the rotation of the removal member 317 relative to the sleeve 310. The removal member 317 also comprises ribs 350 similar to the ribs 340 but not having complementary shapes 341. Consequently, these ribs 350 are shorter than the ribs 340 and have a flat end 351. These flat ends 351 cooperate with flat stops 312 of the end sleeve 310, so as to block in translation the removal member 317 on the distal end 310 of the injection device. In addition, the flat ends 351 and the flat stops 312 are positioned respectively around the removal member 317 and the sleeve 310 such that a rotation of the removal member 317 relative to the sleeve 310 disengages the flat stops 312 from the flat ends 351 and thus allows the removal member 317 to be removed from the distal end 310. The shapes 341 and 311 are located respectively at the distal end of the rib 340 and at the distal end of the end sleeve 310. In the example shown on FIG. 24, the shapes 341 and 311 are circular arcs. These shapes 341 and 311 may nevertheless take any geometrical shape allowing blocking in rotation. Due to the cooperation between these two shapes 341 and 311, the removal member 317 is positioned angularly on the end sleeve 310, and held in this position. Consequently, to remove the removal member 317, in order to remove the protective cap (not shown here), the removal member 317 must be rotated through a certain angle relative to the end sleeve 310, so as to control the removal of the removal member, and therefore of the protective cap. Consequently, if the auto-injector device is dropped, dropping the removal member, i.e. separation between the removal member and the auto-injector device, as well as accidental activation of the auto-injector device, are prevented. The flat ends 351 of the ribs 350 and the flat stops 312 of the end sleeve 310 increase the control exerted on the dropping of the removal member.

This special embodiment can be completed by other characteristics, also shown on FIG. 24. In this alternative, the ribs 340 of the removal member 317 and the outer box 330 comprise elements 342 and 332 intended to cooperate. These elements 342 and 332 are located respectively at the proximal end of the rib 340 and at the distal end of the outer box 330. In the example shown on FIG. 19, the element 342 is a circular arc and the element 332 is a trapezoidal recess. Thus, the element 342 can cooperate with the slopes of the element 332 of the outer box 330, which translation by rotation of the removal member 317 on the outer box 330. More precisely, when the removal member 317 is assembled on the auto-injector device 300, the shape 342 of the rib 340 is positioned against the most proximal portion of the shape 332 of the outer box 330. The slope of the shape 332 facilitates the translation of the removal member by rotation and the release of the shape 342. This therefore facilitates removal of the removal member 317 from the injection device, and therefore removal of the protective cap.

The invention is not limited to the embodiments described and other embodiments will be clearly apparent to those skilled in the art. The removal member can in particular be used for an injection device separate from an injection syringe, for example a cartridge to which a needle is added.

The injection device may also comprise a safety device or an auto-injector device.

The invention claimed is:

1. A removal member for removing a removable needle protective cap for an injection device comprising a needle and the removable needle protective cap, the removal member comprising a housing having a longitudinal axis and being adapted to receive the needle protective cap along an insertion direction, the housing being defined by at least a first support area and a second support area intended to support the needle protective cap housed in the housing, the first support area being carried by a blocking element movable relative to the housing between:

at least a cap insertion configuration, in which orthogonal projections of the first support area and of the second support area are located in a first transverse plane substantially perpendicular to the longitudinal axis of the housing, said orthogonal projections defining a passage presented to the needle protective cap during its insertion in an insertion direction, and said projections being separated by an insertion distance, and a cap blocking configuration, in which the first support area and the second support area are located in separate transverse planes farther away from each other than in the insertion configuration, and in which the orthogonal projections of the first support area and of the second support area in said first transverse plane are separated by a blocking distance less than the insertion distance and adapted to block the translation of the needle protective cap relative to the removal member in a removal direction opposite to the insertion direction, such that the passage presented to the needle protective cap during its insertion in the insertion direction is wider than the passage presented to the needle protective cap in the blocking configuration, thereby blocking the needle protective cap in the removal member by frictional locking of the blocking element, wherein the blocking element moves from the cap insertion configuration to the cap blocking configuration under the action of a pushing element movable relative to the housing between a non-pressed position in which the blocking element is in the cap insertion configuration and a pressed position in which the blocking element is in the cap blocking configuration under the action of the pushing element.

2. The removal member according to claim 1, wherein the blocking element and the removal member have complementary shapes or each has a flat surface defining an axial stop adapted to block the translation of the blocking element relative to the removal member in the direction of removal of the needle protective cap in the removal member.

3. The removal member according to claim 1, wherein the blocking element is movable relative to the housing so as to also take a rest configuration, in which the orthogonal projections of the first support area and of the second support area in a second transverse plane are separated by a rest distance less than the blocking distance.

4. The removal member according to claim 1, wherein the first support area and the second support area are carried by the blocking element.

5. The removal member according to claim 4, wherein the blocking element is a plate folded so as to define two portions extending along each side of an axis for pivoting the portions relative to one another, at least one of the two portions comprising a cap passage opening, and the two portions forming an angle between each other.

6. The removal member according to claim 1, wherein the blocking element is elastically deformable between at least the cap insertion configuration and the cap blocking configuration.

7. The removal member according to claim 1, wherein the pushing element is separate from the cap and is provided with a locking member adapted to immobilize the pushing element relative to the housing in the pressed position.

8. The removal member according to claim 1, comprising at least one flat end complementary to at least one flat stop of a distal end of the injection device, the flat end and the flat stop being adapted to cooperate together so as to block translation of the removal member on the distal end of the injection device.

9. The removal member according to claim 8, wherein the flat end and the flat stop are positioned so that a rotation of the removal member relative to the injection device disengages the flat stop from the flat end.

10. The removal member according to claim 1, comprising a shape complementary to a shape of a distal end of the injection device, the two shapes being adapted to cooperate together so as to block rotation of the removal member on the distal end of the injection device.

11. An injection device comprising the removal member according to claim 1.

12. The injection device according to claim 11, wherein the injection device comprises a safety device to protect the user from being pricked by the needle after use.

13. The removal member according to claim 1, wherein the housing is further defined by a third support area intended to support the needle protective cap to prevent it from pivoting relative to at least one of said first and second support areas in a longitudinal plane, at least when the blocking element moves between its insertion and blocking configurations, the first second and third support areas being arranged staggered each side of the longitudinal axis and in at least two separate transverse planes when the blocking element is in the blocking configuration.

14. The removal member according to claim 13, wherein the blocking element comprises a plate defining at least a first cap passage opening having a contour that defines at least the first support area, wherein the contour of the first passage opening also defines at least one of the second and third support areas.

15. A method for assembling a removal member on an injection device comprising a needle and a removable needle protective cap, the removal member comprising a housing having a longitudinal axis and being adapted to receive the needle protective cap along an insertion direction, the housing being defined by at least a first area and a second area intended to support the cap housed in the housing, the first area being carried by a blocking element movable relative to the housing, the method comprising at least the following steps:

inserting the needle protective cap opposite the housing, in the insertion direction, the blocking element being in a cap insertion configuration, in which orthogonal projections of the first area and of the second area in a transverse plane substantially perpendicular to the longitudinal axis are separated by an insertion distance, and stopping the insertion of the needle protective cap in the removal member, wherein the blocking element takes a cap blocking configuration, in which the first area and the second area are located in separate transverse planes, the orthogonal projections of the first area and of the second area in said transverse plane being separated by a blocking distance less than the insertion distance and adapted to block the translation of the cap relative to the removal member in a removal direction opposite to the cap insertion direction, and wherein the blocking element moves from the cap insertion configuration to the cap blocking configuration by moving the first area relative to the second area via a pushing element, which is moved relative to the housing between a non-pressed position in which the blocking element is in the cap insertion configuration and a pressed position in which the blocking element is in the cap blocking configuration.

16. The method according to claim 15, wherein the needle protective cap is inserted opposite the housing such that the cap exerts a pressure on the blocking element to move the blocking element from a rest configuration, in which the orthogonal projections of the first area and of the second area in the transverse plane are separated by a rest distance less than the blocking distance to the cap insertion configuration, wherein a distance separating said orthogonal projections is increased up to the insertion distance.

17. The method according to claim 15, wherein the pushing element is separate from the needle protective cap and the pushing element is blocked relative to the housing in the pressed position.

* * * * *